US005430208A

United States Patent [19]

Bak et al.

[11] Patent Number: 5,430,208

[45] Date of Patent: * Jul. 4, 1995

[54] METHOD FOR PREPARING 1-CHLORO-1-IODOETHANE

[75] Inventors: Philip I. Bak, Amherst; Gregory P. Bidinger, Akron; Ross J. Cozens, Strongsville; Paul R. Klich, Lyndhurst, all of Ohio

[73] Assignee: The Geon Company, Cleveland, Ohio

[*] Notice: The portion of the term of this patent subsequent to Sep. 6, 2017 has been disclaimed.

[21] Appl. No.: 248,022

[22] Filed: May 19, 1994

Related U.S. Application Data

[63] Continuation-in-part of Ser. No. 35,017, Mar. 22, 1993, Pat. No. 5,345,018.

[51] Int. Cl.$^6$ .............................................. C07C 17/08
[52] U.S. Cl. ...................................... 570/250; 570/249
[58] Field of Search ................................ 570/249, 250

[56] References Cited

U.S. PATENT DOCUMENTS 3,983,187  9/1976  Moczygemba et al. .
4,000,356  12/1976  Weisgerber et al. .
4,361,678  11/1982  Tatemoto et al. .
5,231,154  7/1993  Hung .

FOREIGN PATENT DOCUMENTS 674060  6/1982  United Kingdom .

OTHER PUBLICATIONS

Halogenated Hydrocarbons as Chain Transfer Agents in PVC Polymerization, Society of Plastics Engineers, Apr. 25-28, 1977.
Kharasch et al, JACS 56 pp. 712-714, 1934.

*Primary Examiner*—Johann Richter
*Assistant Examiner*—Kimberly J. Kestler
*Attorney, Agent, or Firm*—Miles B. Dearth; Helen Odar

[57] ABSTRACT

The present invention relates to a method of synthesizing 1-chloro-1-iodoethane by reacting hydrogen iodide with vinyl chloride monomer in the presence of an iodine containing catalyst under certain specified conditions. The resulting product of the reaction is a high yield, high purity 1-chloro-1-iodoethane which is useful as a chain transfer agent in the polymerization of vinyl chloride monomer. The 1-chloro-1-iodoethane formed by the instant invention can be made separately in a conventional synthesis apparatus or the compound can be synthesized in situ in the reaction vessel used for polymerization of vinyl chloride. The in situ process comprises reacting substantially anhydrous hydrogen iodide with an excess of vinyl chloride monomer in the reactor in the presence of an iodine containing catalyst, preferably removing any catalyst and iodine, optionally charging additional vinyl chloride monomer with other polymerization auxiliaries, and initiating the polymerization thereof to form polyvinyl chloride by conventional methods.

16 Claims, No Drawings

METHOD FOR PREPARING 1-CHLORO-1-IODOETHANE

RELATED APPLICATION

This application is a continuation-in-part of Ser. No. 08/035,017, filed Mar. 22, 1993, now U.S. Pat. No. 5,345,018. This application is related to Ser. No. 08/034,981 filed Mar. 22, 1993, entitled, "Method of Synthesizing Poly(Vinyl Chloride) By Means of a Pseudo-Living Radical Polymerization and Product Thereof" by Philip I. Bak, et. al.

BACKGROUND OF THE INVENTION

1. Field of Invention

The present invention relates to a simple, efficient method of synthesizing 1-chloro-1-iodoethane. More particularly, the process of the present invention comprises the addition of substantially pure and anhydrous hydrogen iodide to vinyl chloride monomer in the presence of an iodine containing catalyst. Under these conditions, the reaction results in 1-chloro-1-iodoethane. 1-Chloro-1-iodoethane is especially effective as a chain transfer agent for the polymerization of vinyl chloride in a process mimicking a living radical polymerization as explained in our co-pending application, referenced above. The 1-chloro-1-iodoethane chain transfer agent formed according to the method of the instant application can be added to a vinyl chloride polymerization system separately after the 1-chloro-1-iodoethane is formed. Alternatively, the 1-chloro-1-iodoethane may be generated in the reaction vessel prior to the polymerization of the vinyl chloride monomer. With the use of 1-chloro-1-iodoethane, a poly(vinyl chloride) polymer having low molecular weight (Mn generally less than 30,000), low polydispersity (generally less than 2.2), and good thermal stability is formed.

2. Description of the Art

The addition of hydrogen iodide to vinyl chloride was first described by Kharasch and Hannum in an article in 1934. The article, entitled "The Peroxide Effect in the Addition of Reagents to Unsaturated Compounds IV. The Addition of Halogen Acids to Vinyl Chloride", J. American Chem. Soc., 56, (1934) p. 712 described the addition of various halogen acids such as hydrogen iodide to vinyl chloride. In particular, Kharasch et. al. discuss the addition of 0.12 moles of hydrogen iodide to 0.1 mole of vinyl chloride in a reactor. By these experiments, Kharasch et. al. were studying the effects of peroxides on reactions which occur via a carbocation process as opposed to a free radical process.

An attempt was made to reproduce the work of Kharasch and Hannum under modern experimental conditions. Using the Kharasch procedure, there was no 1-chloro-1-iodoethane synthesized.

However, applicants have discovered a novel process for synthesizing 1-chloro-1-iodoethane. Accordingly, a primary object of the present invention is to synthesize 1-chloro-1-iodoethane.

SUMMARY OF THE INVENTION

In accordance with the invention there is provided the addition of substantially anhydrous hydrogen iodide to vinyl chloride monomer in the presence of an iodine containing catalyst under specified conditions. The reaction yields 1-chloro-1-iodoethane which is useful as a chain transfer agent for the free radical polymerization of vinyl chloride monomer. The 1-chloro-1-iodoethane formed by the instant invention can be made separately in a conventional synthesis apparatus or the compound can be synthesized in situ in the reaction vessel used for polymerization of vinyl chloride. The in situ process comprises reacting substantially anhydrous hydrogen iodide with an excess of vinyl chloride monomer in the reactor in the presence of an iodine containing catalyst, optionally removing any catalyst, optionally charging additional vinyl chloride monomer with other polymerization auxiliaries, and initiating the polymerization thereof to form polyvinyl chloride by conventional methods. Auxiliaries refer to such conventional components as water, dispersants, surfactants and initiator. Thus, the 1-chloro-1-iodoethane can be present at the beginning of polymerization or introduced in any manner such as by proportioning (metering) at desired rate(s) during the polymerization.

DETAILED DESCRIPTION OF THE INVENTION

When 1-chloro-1-iodoethane is synthesized in a polymerization reaction vessel by the in situ method in the same vessel where initiation of polymerization of vinyl chloride monomer occurs, hydrogen iodide and catalyst are combined with an excess of the stoichiometric amount of vinyl chloride. When using an organoiodide as catalyst, the organoiodide can remain in the polymerization vessel as it would not interfere in the vinyl chloride polymerization to any appreciable extent and may act as a chain transfer agent to a minor extent. In the case where an inorganic iodide is used as a catalyst, it is preferred that after synthesis of 1-chloro-1-iodoethane, water and sodium thiosulfate are added to the reactor, fitted with a bottom valve, and drawn from the vessel thereby removing iodine via the water layer.

After synthesis of 1-chloro-1-iodoethane and any necessary work up of the product, any of the conventional aqueous or bulk polymerization methods can be conducted in the vessel in which the chain transfer agent has been synthesized. Suitable polymerization methods for making polyvinyl chloride include: mass, suspension, micro-suspension, dispersion or emulsion processes. A mass process is described in U.S. Pat. No. 3,522,227, incorporated herein by reference. A phase inversion process resulting in a suspension type PVC resin may also be used and is disclosed in U.S. Pat. No. 3,706,722 incorporated herein by reference. An emulsion polymerization process is disclosed in U.S. Pat. No. 4,186,259, incorporated herein by reference.

The subject reagent of this invention is vinyl chloride. Preferably, the vinyl chloride should be of high purity and dryness. Moreover, a slight excess of vinyl chloride monomer over hydrogen iodide is recommended to ensure complete consumption of hydrogen iodide. Polyvinyl chloride is a worldwide commodity. The type and amount of commercially available vinyl chloride is selected by anyone having ordinary skill in the art.

The iodine catalyst can be any iodine containing compound which is capable of liberating molecular iodine and the residue of which will not in itself adversely react with vinyl chloride or hydrogen iodide. The iodine catalyst can be any organic iodide or inorganic iodide. The organoiodides include but are not limited to alkyl iodides, like methyl iodide, iodoform, diiodomethane, 1,2-diiodoethane and iodoacetonitrile;

alkylhaloiodides such as chloroiodomethane, 1-chloro-1,2-diiodoethane, 1,3-dichloro-1-iodopropane, 4-chloro-4-iodobutyronitrile, 3-chloro-3-ethyliodopropionate; aromatic iodides, such as benzyl iodide and 1-chloro-1-iodo-3-phenyl propane. Inorganic iodides which can be used include but are not limited to potassium iodide, sodium iodide, lithium iodide, BrI, ClI and molecular iodine. Generally, an effective amount of iodine containing catalyst is from about 0.001 to about 5 moles of catalyst per mole of HI. Preferably, a minimum effective amount of catalyst is used such as 0.04 to 1 mole per mole HI. When an inorganic iodide catalyst is employed, better yields are obtained with the addition of an oxidizing agent such as sodium persulfate, sodium hypochlorite, potassium permanganate, ammonium persulfate, perchloric acid, potassium perchromate, and the like. The equivalents of oxidizer per mole catalyst are calculated following ordinary stoichiometry. Molecular iodine ($I_2$) and diodoethane work especially well and are the most preferred iodine catalysts.

The synthesis is carried out in any reaction vessel suitable for the reaction of vinyl chloride monomer and no special techniques are needed. On a commercial scale, vinyl chloride as well as volatile iodocompounds are typically contained in a closed system with preventive measures taken to ensure no release into the atmosphere.

The reaction temperature is generally from about $-75°$ C. to $100°$ C. Most preferably, the reaction temperature is from about $-50°$ C. to $-45°$ C. Significant yields can be obtained within approximately one to five hours of reaction time. Completion is indicated when the reactor pressure drops to the vapor pressure of the vinyl chloride. Using methods exemplified below, yield in excess of 80 percent is obtainable. The resulting 1-chloro-1-iodoethane may be purified as described below.

Any remaining iodine, which hinders vinyl chloride monomer polymerization, should be removed from the 1-chloro-1-iodoethane which is formed. If an organoiodide is used as the catalyst then the reaction product is preferably purified by distillation when isolated product is desired. If molecular iodine or an inorganic iodide is used as catalyst, then the 1-chloro-1-iodoethane may be purified simply by washing with sodium thiosulfate, followed by washing with water and finally drying the product over an anhydrous drying agent, e.g., magnesium sulfate. It is suggested that the 1-chloro-1-iodoethane should be stored in the dark over copper turnings to inhibit degradation.

EXAMPLE 1

Synthesis with $I_2$ Catalyst

A 1-liter three-necked flask, equipped with nitrogen ("$N_2$") purge, stirrer, and cold finger condenser was assembled. The flask was immersed in a dry ice/acetone bath and the cold finger filled with the same. The flask was flushed with $N_2$. 294.3 grams vinyl chloride monomer ("VCM") (4.71 moles) were slowly added from a vessel via Teflon tubing to the flask. The VCM condensed upon contact with the cooled flask walls. 105.2 grams hydrogen iodide (HI) (0.82 moles) were slowly bubbled through the VCM via Teflon tubing. Then, approximately 3 grams (0.01 moles) iodine crystals were added. The contents of the flask were stirred at dry ice/acetone temperature for three hours and then the bath was removed. The cold finger was maintained for an additional two hours. Unreacted reagents were permitted to evaporate as the reaction mixture warmed to room temperature. 131.0 grams of the product were isolated as a purple liquid. The yield of 1-chloro-1-iodoethane was 83%.

The purple liquid was found to lose its color in the presence of sodium thiosulfate. All of the liquid was added to a separatory funnel. An equal amount of 0.1N sodium thiosulfate was added. With continued shaking, a pale yellow organic layer (bottom layer) was obtained. The organic liquid was dried over magnesium sulfate.

Upon standing, the filtered material began to turn pink. Copper filings were added and two days later, the product was found to be a very pale yellow. A week later the color had not changed.

A $^{13}C$ NMR spectrum was run on the purified material in $CDCl_3$. Sharp, narrow peaks were found at 22.08 and 35.67 ppm. Very small peaks were found at approximately 85 and 130 ppm. The spectrum was identified as 1-chloro-1-iodoethane.

Comparative Example 2

The reaction was carried out in a 1 liter glass pressure vessel, equipped with an agitator according to the method of Kharasch and Hannum discussed above. The vessel was placed under an atmosphere of nitrogen. When the vessel was cooled to around $0°$ C., vinyl chloride monomer (125 grams, 2 moles) was added. With the temperature held at or below $0°$ C., approximately 245 grams (1.9 moles) of HI vapor were transferred into the vinyl chloride using a Teflon line. The colorless mixture of liquid was then stirred and allowed to warm to room temperature over a period of approximately four hours. During that time, the reaction mixture became a pale pink in color. On subsequent evaporation of excess reagents, no measurable yield of 1-chloro-1-iodoethane was obtained. The fact that no 1-chloro-1iodoethane was obtained using the Kharasch et. al. method reaffirms that an iodine containing catalyst is necessary to render 1-chloro-1-iodoethane.

EXAMPLE 3

Synthesis with Organo Iodide Catalyst

Synthesis of 1-chloro-1-iodoethane was carried out in the presence of an organoiodide catalyst in Example 3. To a pressure tube cooled in dry ice/acetone was added 38.4 grams of vinyl chloride and 61.7 grams of HI. The solution was pale pink to yellow in color. To this mixture was added 5.3 grams of 1,2-diiodoethane. The tube was sealed and removed from the coolant bath. The tube remained at room temperature for 24 hours. The tube was then cooled in dry ice/acetone and unsealed. VCM and HI were vented off. The crude product was transferred to a separatory funnel and 50 ml of 0.1N sodium thiosulfate was added which removed the purple color. About 1 gram of anhydrous magnesium sulfate was added and the crude product yield was 59.4 grams which was 64.7% of theoretical yield. An NMR spectrum was obtained with sharp, prominent peaks at 21.95 and 35.74 ppm, confirming that the product was 1-chloro-1-iodoethane.

EXAMPLE 4

Using Inorganic Iodide Catalyst

Synthesis of 1-chloro-1-iodoethane was carried out in the presence of an inorganic iodide catalyst in Example 4. To a pressure tube cooled in dry ice/acetone was added 36.8 grams of vinyl chloride and 58.2 grams of HI. The solution was pale pink to yellow in color. To this mixture was added 6.2 grams of KI in 10 grams H$_2$O. The tube was sealed and removed from the coolant bath. The tube remained at room temperature for 24 hours. The tube was then cooled in a dry ice/acetone bath and unsealed. VCM and HI were vented off. The amount of crude 1-chloro-1-iodoethane obtained was 21.33 grams.

EXAMPLE 4a

Oxidizing Agent with Catalyst

The yield of product from Example 4 was improved on the addition of oxidizing agent. In a repeat of example 4, 41.4 grams of vinyl chloride and 57.6 grams of HI were combined into the cooled pressure tube. To this tube was added 6.2 grams of KI and 3.06 grams of Na$_2$S$_2$O$_8$ along with 30 grams of H$_2$O. The same reaction procedure of example 4 was followed. The amount of crude 1-chloro-1-iodoethane obtained was 30.43 grams.

From the foregoing description, one skilled in the art can easily ascertain the essential characteristics of this invention and without departing from the spirit and scope thereof can make various changes and modifications of the invention and adapt it to various usages and conditions.

We claim:

1. A process for preparing 1-chloro-1-iodoethane comprising combining substantially anhydrous hydrogen iodide and vinyl chloride monomer in a vessel at a temperature of from −75° C. to 100° C. and adding from 0.001 to 5 moles of a catalyst per mole of hydrogen iodide, wherein said catalyst is selected from the group consisting of organo iodide and inorganic iodide.

2. The process of claim 1 wherein said iodine containing catalyst is an organoiodide selected from the group consisting of an alkyl iodide, haloalkyliodide, and an aromatic iodide.

3. The process of claim 2 wherein said iodine containing catalyst is selected from the group consisting of methyl iodide, iodoform, diodomethane, 1,2-diiodoethane, chloroiodomethane, 1-chloro-1,2-diiodoethane, 1,3-dichloro-1-iodopropane, 4-chloro-4-iodobutyronitrile, ethyl 3-chloro- 3-iodopropionate, benzyl iodide, 1-chloro-1-iodo-3-phenyl propane and iodoacetonitrile.

4. The process of claim 1 wherein said iodine containing catalyst is an inorganic iodide.

5. The process of claim 4 wherein said iodine containing catalyst is selected from the group consisting of potassium iodide, sodium iodide, lithium iodide, BrI, and ClI.

6. The process of claim 4 further comprising an oxidizing agent.

7. The process of claim 6 wherein said oxidizing agent is selected from the group consisting of sodium persulfate, sodium hypochlorite, potassium permanganate, perchloric acid, and potassium perchromate.

8. A process for synthesizing 1-chloro-1-iodoethane in situ in a polyvinyl chloride polymerization reactor at a temperature of from −75° C. to 100° C. comprising reacting substantially anhydrous hydrogen iodide with a stoichiometric excess of vinyl chloride monomer in said polymerization reactor in the presence of from 0.001 to 5 moles of an iodine containing catalyst per mole of hydrogen iodide, thereaafter in introducing water, and any optional additional vinyl chloride monomer, and initiating thereafter vinyl chloride polymerization to form polyvinyl chloride and wherein said catalyst is selected from the group consisting of organo iodide and inorganic iodide.

9. The process of claim 8 wherein said iodine containing catalyst is present in an amount of from 0.001 to 5 moles per mole of hydrogen iodide.

10. The process of claim 8 wherein said iodine containing catalyst is an organoiodide selected from the group consisting of an alkyl iodide, haloalkyliodide, and an aromatic iodide.

11. The process of claim 10 wherein said iodine containing catalyst is selected from the group consisting of methyl iodide, iodoform, diodomethane, 1,2-diiodoethane, chloroiodomethane, 1-chloro-1,2-diiodoethane, 1,3-dichloro-1-iodopropane, 4-chloro-4-iodobutyronitrile, ethyl 3-chloro- 3-iodopropionate, benzyl iodide, 1-chloro-1-iodo-3-phenyl propane and iodoacetonitrile.

12. The process of claim 8 wherein said iodine containing catalyst is an inorganic iodide and said process further comprises the step of adding water and optional sodium thiosulfate to said reactor following reaction of hydrogen iodide and vinyl chloride, followed by removal of said water prior to initiation of polymerization.

13. The process of claim 12 wherein said iodine catalyst is selected from the group consisting of potassium iodide, sodium iodide, lithium iodide, BrI, and ClI.

14. The process of claim 13 wherein said reaction is carried out in the presence of an oxidizing agent.

15. The process of claim 14 wherein said oxidizing agent is selected from the group consisting of sodium persulfate, sodium hypochlorite, potassium permanganate, perchloric acid, and potassium perchromate.

16. The process of claim 15, wherein said temperature is in the range of about −75° C. to about 25° C.

* * * * *

UNITED STATES PATENT AND TRADEMARK OFFICE
CERTIFICATE OF CORRECTION

PATENT NO. : 5,430,208
DATED : July 4, 1995
INVENTOR(S) : Ross J. Cozens, et. al.

It is certified that error appears in the above-indentified patent and that said Letters Patent is hereby corrected as shown below:

Title page, [*] Notice: should read: The portion of the term of this patetn subsequent to Sept. 6, 2011 has been disclaimed.

Signed and Sealed this

Twelfth Day of September, 1995

Attest:

BRUCE LEHMAN

Attesting Officer

Commissioner of Patents and Trademarks